United States Patent [19]

Heller

[11] Patent Number: 4,824,776

[45] Date of Patent: Apr. 25, 1989

[54] METHOD FOR INCREASING THE SENSITIVITY OF NUCLEIC ACID HYBRIDIZATION ASSAYS

[75] Inventor: Michael J. Heller, Poway, Calif.

[73] Assignee: Molecular Biosystems, Inc., San Diego, Calif.

[21] Appl. No.: 759,047

[22] Filed: Jul. 25, 1985

[51] Int. Cl.[4] .................... C12Q 1/68; G01N 33/566
[52] U.S. Cl. ...................................... 435/6; 435/803; 436/501; 536/27; 935/2; 935/8; 935/9; 935/10; 935/78
[58] Field of Search .................... 435/6, 803; 436/501, 436/518, 531; 536/27; 935/2, 8, 9, 10, 78

[56] References Cited

U.S. PATENT DOCUMENTS

| | | | |
|---|---|---|---|
| 4,430,496 | 2/1984 | Abbott | 536/27 |
| 4,486,539 | 12/1984 | Ranki et al. | 436/804 X |

FOREIGN PATENT DOCUMENTS

| | | |
|---|---|---|
| 0200057 | 11/1986 | European Pat. Off. |
| 2139349 | 11/1984 | United Kingdom . |

OTHER PUBLICATIONS

Green et al, "Reassociation Rate Limited Displacement of DNA Strands", Nucleic Acids Res. 9(8), 1905–1918 (1981).

Primary Examiner—Esther M. Kepplinger
Assistant Examiner—Richard Wagner
Attorney, Agent, or Firm—Pretty, Schroeder, Brueggemann & Clark

[57] ABSTRACT

An improvement in the sensitivity of hybridization assays for detecting polynucleotide target sequences is provided by selective dehybridization of the bound portion of the probe, separation of the dehybridized portion from the support and the residual sample, and concentrating the separated probe before detecting its presence by means of its reporter group. The concentration step can be carried out by adsorption of the dehybridized probe onto a basic ion exchange material. A displacer sequence having greater binding affinity for the target polynucleotide sequence may be used to dehybridize the bound probe portion for subsequent concentration.

14 Claims, No Drawings

METHOD FOR INCREASING THE SENSITIVITY OF NUCLEIC ACID HYBRIDIZATION ASSAYS

FIELD OF INVENTION, BACKGROUND AND PRIOR ART

The field of this invention involves a hybridization assay system for detecting target polynucleotide sequences in deoxyribonucleic acid (DNA) and/or ribonucleic acid (RNA) samples. More specifically, the invention is concerned with a method for increasing the sensitivity and where necessary the selectivity of the hybridization assay using labelled oligonucleotide probes to detect specific target sequences.

Hybridization assays may be employed for the detection and identification of DNA or RNA sequences. Published methods as used particularly in recombinant DNA research are described in *Methods in Enzymology*, Vol. 68, pp. 379-469 (1979); and Vol. 65, Part 1, pp. 468-478 (1968). One such method involving a preliminary separation of the nucleic acid fragments by electrophoresis is known as the "Southern Blot Filter Hybridization Method." See Southern, *J. Mol. Biol.* (1975) 98: 503. Hybridization probe methods for detecting pathogens are described in U.S. Pat. No. 4,358,539.

There has been a recognized need for improving hybridization assays. Instead of radiolabelled probes, which can require several days for development of the X-ray film, detection by means of luminescent-labelled probes are claimed to have advantages. (See published European patent application No. 0 070 687.) A procedure for obtaining increased sensitivity from luminescent-labelled probes is disclosed in published European patent application No. 0 070 685. Two probes are employed, having respectively a chemiluminescent catalyst and an absorber/emitter (fluorophore) moiety. Upon hybridization to the appropriate polynucleotide target sequence, the light signal from the probes is shifted to a higher wavelength. This wavelength shifting leads to an improved and more sensitive assay system.

As an alternative to employing long double-stranded probes resulting from recombinant DNA cloning procedures, short synthetically produced single-stranded probes have been described. (See, for example, PCT Publication No. WO 84/03285). Such short probes, which normally contain from 18 to 40 nucleotides, are available from Molecular Biosystems, Inc., San Diego, Calif. Typically, such short probes can be labelled with biotin, enzymes, and fluorescent reporter groups. These probes can be constructed complementary to a unique sequence of the target DNA or RNA fragments. Furthermore, they are in stable single-stranded form and renaturation cannot interfere with the assay. Short labelled DNA probes as described above, in principle, should be useful in developing rapid and convenient non-radioisotope DNA hybridization assays. With existing procedures, concentrations of the hybridized labelled probe can be detected down to about $10^{-16}$ to $10^{-17}$ moles under ideal conditions. For most of the potentially important clinical applications of DNA probes (infectious diseases, latent virus, genetic disorders, etc.), it will be necessary to have sensitivity levels of at least $10^{-18}$ moles and lower. With present techniques the inherent sensitivities possible with non-radioisotope labels such as fluorophores and enzymes are still limited by a wide variety of problems. In the case of fluorescent labels, background fluorescence and light scattering from the hybridization support materials (nitrocellulose and nylon filters, polystyrene beads, etc.) lead to significant loss of inherent sensitivity. In the case of enzyme labels, non-specific binding of the labeled probe and interfering stains and colors from sample material can limit ultimate sensitivity of this label. Other problems superimposed upon those metioned above lead to further losses of sensitivity and limit the practicality of these systems for clinical diagnostic purposes.

SUMMARY OF INVENTION

The present invention provides a method for ultrasensitive detection of reporter group-labelled DNA probes used in hybridization assay systems. The method is particularly applicable to fluorescently-labelled short probes, but should also provide improvements for enzyme-labelled probes. In the case of fluorescent probes, greater sensitivities can be obtained than with any prior hybridization assay system, viz. as little as $10^{-18}$ moles of probe and below can be detected.

The method of this invention utilizes a probe concentration or refocusing procedure. After the basic hybridization procedure has been carried out and the support matrix (nitrocellulose, for example) has been washed free of unbound probe, instead of attempting to detect the presence of bound probe directly as in conventional systems, the probe is subjected to a dehybridization procedure. Dehybridization can be carried out by treatment with denaturing agents (heat, urea, etc.) which will release the bound probe from the support matrix and liberate it into the aqueous solution. The bound probe can also be liberated in a much more selective fashion using a second DNA probe which is called a "displacer probe." In either case the liberated probe, in solution, is now concentrated or refocused by addition of a small amount of an appropriate material with high affinity for the probe.

In one preferred procedure, after dehybridization from the support matrix (nitrocellulose or nylon filters), the fluorescently labelled probe is adsorbed onto a small amount of adsorbent beads or particles having high affinity for oligonucleotides. For example, the adsorbent may comprise beads of porous, crosslinked dextran or glass particles substituted with positively charged groups. Such adsorbents are available commercially and are improved substrates for fluorescent probe detection in particular. For example, anion exchange materials such as diethylaminoethyl (DEAE) or quaternary aminoethyl (QAE) dextran and glass beads have extremely high affinity for labelled oligonucleotide probes. This high affinity is due to the electrostatic or ion exchange interaction between the polyanionic nucleotide and the high positive charge density on the beads. These beads have been found to provide extremely low background fluorescence and significantly less light scattering effects than nitrocellulose or nylon filter material. Most importantly, the dehybridization and adsorption onto a small amount of adsorbent material concentrates (10-5000 fold) the fluorescent probe onto a substrate much more favorable for fluorescent (epifluorescent) detection. In summary, the fluorescent signal is now highly concentrated, background is significantly reduced, and interferences from the hybridization support material (nitrocellulose filters, other sample components on the filters, etc.) have been eliminated.

While the specific procedures discussed above are preferred, within the broader context of the improved method of this invention other concentration or focusing procedures can be employed. Moreover, the probes can be used which are labelled with other types of reporter groups (i.e., enzymes or luminescent groups). With such modifications, improvements in detection sensitivity can also be obtained in accordance with the principles of this invention.

DETAILED DESCRIPTION

In practicing the method of this invention, the DNA or RNA test samples containing target sequences may be prepared by any one of a number of known procedures and attached to suitable immobilization support matrix. For example, such procedures are described in *Methods in Enzymology*, Vol. 68, pp. 379–469 (1979); and Vol. 65, Part 1, pp. 468–478 (1980), U.S. Pat. No. 4,358,539; and in published European patent applications Nos. 0 070 685 and 0 070 687. Any of the usual supports can be employed, such as nitrocellulose filters, Zetabind ® (nylon) filters, polystyrene beads, etc.

The following is a general description of the basic procedures for carrying out the hybridization of labelled short DNA probes to samples of target DNA immobilized on nitrocellulose and Zetabind ® filters. With minor variations the procedure is applicable for hybridizing radioisotope ($32p$), biotin, enzyme, lumiphore, and fluorophore labelled short probes.

Buffers and Solutions

All buffers should be made with double-distilled water. Concentrated stock solutions should be diluted with double-distilled water. Filter, where indicated, through $0.45\mu$ nitrocellulose.

20 SSPE BUFFER. Dissolve 210 g NaCl, 27.6 g $NaH_2PO_4 \cdot H_2O$, 7.4 g $Na_2$ EDTA, and approximately 8.3 ml of saturated NaOH (to pH 7.0). Adjust volume to one liter, filter, autoclave and store at room temperature.

20 SSC BUFFER. Dissolve 175.3 g NaCl and 88.2 g sodium citrate in 800 ml water. Adjust pH to 7.0 with a few drops of concentrated NaOH. Adjust volume to one liter, filter, autoclave, and store at room temperature.

0.3M HaOH. Store at room temperature.

1M and 2M Ammonium Acetate. Filter and store at room temperature.

4×BP. Dissolve 2 g each bovine serum albumin, crystalline Pentex Fraction V., and polyvinylpyrrolidone, average mol. wt.=40,000, in 100 ml water. Filter and store at $-20°$ C. in small aliquots.

10% (W/V) Sodium Dodecyl Sulfate (SDS). Store at room temperature.

Other Materials

Nitrocellulose filters (Schleicher & Schuell, Keene, NH, #BA85) or Zetabind membranes (AMF, Meriden, CT, #NM511-01-04-5SP).

Whatman 3MM chromatography paper.

DEAE-cellulose. Whatman DE52, precycle according to the manufacturer.

Dot blot filtration apparatus (HYBRI·DOT ™, BRL, Bethesda, MD; Minifold II, S & S, Keene, NH; BIODOT ™, Bio-Rad Laboratories, Richmond, CA.)

Water baths.

Vacuum pump.

Vacuum oven.

Automatic micropipets and tips.

Disposable tuberculin syringes (1 ml).

Glass wool.

Sample Preparation

The method of fixing target DNA to nitrocellulose filters will vary depending on the source of the sample. Purified DNA may be bound by filtration by Southern blotting, by Dot blotting. Virus-infected whole cells can be fixed to nitrocellulose by spotting followed by denaturation.

The following procedure is suitable for binding the DNA to nitrocellulose filters. It should be modified according to the needs of the individual experiment. The following steps are performed at room temperature unless indicated otherwise.

NOTE: Nitrocellulose and nylon filters should be stored in a dry cool place and protected from fumes of organic solvents. Handle the filters with gloves.

1. Cut the nitrocellulose or nylon to fit the dot blot apparatus and wet the filters in hot (approximately 60° C.) sterile water. Make certain that the sheet is completely wet, then rinse it several additional times with hot clean water.

2. Soak the sheet in 6×SSC buffer while preparing the samples.

3. Resuspend DNA in 0.1 ml 0.3M NaOH and boil for 5 minutes.

4. Immediately chill the sample in ice and add 0.1 ml 2M Ammonium Acetate. Mix well.

5. Clamp sheet in the dot blot apparatus, apply a gentle vacuum and wash the wells with 200 $\mu$l 6×SSC.

6. Decrease the vacuum and add the samples. A sample should take several minutes to filter in order for the DNA to bind quantitatively.

7. After the samples have filtered through, wash the wells as in Step 5.

8. Remove the filter from the apparatus, wash it in 6×SSC, and air dry.

9. Place the filter between the folded sheets of Whatman 3MM paper and bake in a vacuum oven for one hour at 80° C. Nylon support should be dried for 15–30 minutes at 80° C.

10. Filter sheets prepared thus may be stored dry at 4° C. in sealed plastic bags.

Hybridization Detection

1. Prehybridize the filter in 5×SSPE, 1×BP, and 1% SDS for 5 minutes at 50°±2° C.

2. Transfer the filter to a boilable polyethylene bag, add 50 $\mu$l per cm$^2$ of 5×SSPE, 1×BP, 1% SDS, containing ~5–500 ng/ml of appropriately labelled probe and heat-seal the bag. Incubate for 30 minutes at 50°±2° C. with gentle agitation.

3. After the incubation, open the bag and discard the buffer into an appropriate waste container. Wash the filter as follows, using a large excess of 1×SSPE, 1% SDS; three times at 37° C. for five minutes each followed by one wash at 50° C. for one minute.

4. At this point different procedures can be carried out depending upon the nature of the label and detection system (radioisotope, enzyme/color dye system, etc.). With regard to the further teaching in this patent application and in reference to fluorescently labeled probes in particular, the filters would be washed one time with 1×SSPE. At this point procedures discussed later in the application apply.

The probe is designed and selected to provide a complementary sequence for binding to the target DNA or RNA sequences. Short-chain probes are preferred, such as those containing from 10 to 50 nucleotide units, and a single complementary sequence to a characterizing sequence of the target DNA or RNA. Longer probes such as probes containing in excess of 200 nucleic acid units may contain a plurality of complementary sequences. Such long probes may be used to obtain some of the advantages of the present invention. Probes prepared by nucleotide synthesis which contain from 18 to 30 nucleic acid units are particularly desirable. Methods for synthesizing and labelling such short probes are described in for published PCT Application No. WO 84/03285.

As in prior practice, any one of a number of different kinds of reporter groups or labels may be attached to the probes. Radioactive labels which may be employed include $^{32}P$, $^{3}H$, $^{14}C$ labelled probes. However, labels generating some fluorescent or colorometric response are preferred, as described in the published European patent application No. 0 070 687. In particular, it is preferred to employ fluorescent labels. Fluorescent labelling is described in PCT Publication No. WO 84/03285. The fluorescent labels may include fluorescein, Texas Red, Lucifer Yellow, pyrene, lanthanide complexes, etc. The preferred probe is one containing a single fluorescent label attached to a complementary sequence of 18 to 30 nucleic acid units. However, the use of two or more fluorophore labels per probe is not excluded, particularly in cases where fluorophore combinations effect a condition for improved detection of fluorescent signal.

The novel steps of the present invention begin following the hybridization and removal of the unbound probe from the initial support matrix (nitrocellulose, etc.). In the event that the concentration of the hybridized probe is sufficient to provide appropriate selectivity and sensitive detection, the method of the present invention need not be employed.

The first step in utilization of the new methodology involves the dehybridization of the labelled probe from the initial support matrix. Dehybridization may be effected by known denaturation procedures, which cause double-stranded nucleic acids to separate into single-stranded form. For example, dehybridization may be carried out by heating the support matrix/target DNA/hybridized labelled probe in a small amount of water or dilute buffer (0.1 to 1X SSPE or SSC) to a temperature sufficient to produce denaturation. In general, effective denaturing temperatures (also called melting temperatures) are in the range from 60° to 90° C. The required temperature depends on the length and "GC" (Guanine & Cytosine) content of the probe. In an alternative procedure, an appropriate buffered solution containing a denaturing agent such as urea or formamide can be used to cause dehybridization of the probe. For example, a 6 molar urea (0.1X−1X SSPE or SSC) solution is effective in dehybridizing the probe at room temperature (20°−30° C.). A variety of general procedures and agents exist for causing dehybridization of the probe from the support. In general, selection is based on the ease and speed of the procedure and the important requirement that it not interfere or inhibit the second stage of the process, i.e., where the labelled probe is adsorbed and concentrated onto a suitable material for detection.

In an alternative procedure which is not known to have been previously employed, the dehybridization of the labelled probe is effected by means of a "displacer probe." The displacer comprises a single-stranded oligonucleotide sequence including the same sequence as the labelled probe with an additional sequence on one side, the additional sequence being complementary to a corresponding sequence on the target strand to which the probe is bound. The additional sequence should be of sufficient length to enable the displacer to preferentially bind to the target sequence near the probe and then efficiently displace the probe. For example, the additional sequences may contain from 10 to 20 nucleic acid units and may be provided on either side of the labelled probe sequence. By way of more specific example, where the hybridized labelled-probe contains from 18 to 30 nucleic acid units, the displacer may correspondingly contain from about 28 to 50 nucleic acid units. Longer displacer probes can also be employed.

In using the displacer, it may be applied in aqueous buffered solution to the hybridized probe. For example, the supported hybridized probe may be immersed in a solution of the displacer. The typical concentrations will range from about $1 \times 10^{-13}$ to $1 \times 10^{-11}$ moles of the displacer per 50 microliters of solution (0.1 to 5.0×SSPE or SSC). The displacement may be carried out at room temperatures (viz. 20°–30° C.) in less than 30 minutes. In general, the conditions employed are optimized to allow efficient hybridization of the displacer probe/dehybridization of the labelled probe, and as minimal leaching of non-specific bound labelled probe as possible.

This displacement procedure has a further important advantage in that it increases selectivity. During hybridization some of the labelled probe may have become bound to components of the sample other than the target sequence. Where such extraneous binding has occurred, a false positive indication can be obtained if the non-specifically bound labelled probe is detected in the sample. By using the displacer, however, displacement occurs for only that portion of the probe specifically hybridized to the target sequence. Thus, the displacer probe gives double specificity to the assay procedure.

With the preferred procedures described above, the bound labelled probe can be dehybridized from the support material and obtained in the form of an aqueous solution. Direct detection of the labelled probe in the aqueous solution is usually not feasible because the concentration of the labelled probe is extremely low. However, by concentrating and focusing the dehybridized probe, it can be effectively detected at concentrations down to $10^{-18}$ moles and below.

In one preferred procedure, the dehybridized probe is adsorbed from the solution onto an anion exchange material which provides positively charged groups for binding the probe. Weak basic anion exchange materials containing substituted amino groups may be employed as well as strongly basic anion exchange materials with quaternary amino groups.

It is presently believed, however, that quaternary amino type materials are the most desirable.

Anion exchange materials suitable for use in the method of this invention are available commercially. Such materials can be prepared from substrates comprising cross-linked dextran or glass. Such materials are usually in the form of porous beads or granules of ultra-fine particle sizes (viz. 50–200 micron diameter). Anion exchange materials based on cross-linked dextran are available from Pharmacia (Uppsala, Sweden). These products are in the form of small, generally spherical beads with varying degrees of porosity depending on the extent of cross-linking of the dextran. Quaternary amino beads are sold by Pharmacia under the trademark "QAE-Sephadex." The quaternary groups are attached to the dextran substrate as quaternary amino-ethyl groups. Other amine-type beads are also supplied by Pharmacia under the trademark "DEAE-Sephadex." These products contain diethylaminoethyl groups attached to the dextran.

While either DEAE-Sephadex or QAE-Sephadex can be used with the method of the present invention, it is presently believed that "QAE-Sephadex" is preferred. Further, a presently preferred adsorbent is "QAE-Sephadex A-25," which is a more highly cross-linked dextran substrate than "QAE-Sephadex A-50." Greater cross-linking restricts swelling of the beads and this is believed advantageous since an essentially surface adsorption is desired for purposes of the present invention. However, some penetration of the probe into the beads is not objectionable. Typically, the Sephadex beads may have average sizes of around 100 microns.

Where an adsorbent is employed for the dehybridized probe as described above, it is desirable that the adsorbent be formed of a substance which does not interfere with the fluorescent analysis. Fortunately, it has been found that both anion exchange dextran beads and glass beads have excellent background properties with reference to fluorescent analysis. Neither the dextran nor the glass interferes with the analysis. These adsorbents have very low background fluorescence and produce minimal light scattering effects.

Porous glass beads are also available which have anion exchange properties, being either weak ion exchangers with attached amine groups or strong ion exchangers with attached quaternary amino groups. For example, such products can be obtained from Pierce Chemical Company, Rockford, Ill. The size of the beads may range from about 50 to 200 microns. This type of product is sometimes referred to as "controlled pore glass." Diethylaminoethyl (DEAE) controlled pore glass is available from Pierce Chemical Company as well as quaternary aminoethyl (QAE) controlled pore glass. One specific product which may be employed is sold by Pierce as Product No. 23514 CPG/QAE Glycophase Pore Glass.

For use in conjunction with fluorescent detection equipment, such as an epifluorescent microscope, it may be desirable to prepare glass slides, glass tips, or fiber optic tips which provide a surface that is suitable for binding the dehybridized probe. Amine groups can be attached to the silica glass by a silanization process. See, for example, Lowe and Dean, "Affinity Chromatography," pp. 217 and 256 (1974), John Wiley & Sons, New York. As initially attached, the nitrogen groups will be in the form of primary amine groups. By well-known procedures, such primary amine groups can be easily converted to secondary, tertiary, or quaternary amino groups.

To achieve effective concentration of the dehybridized probe, it is preferred to use minimal amounts of the adsorbent. For example, employing Sephadex QAE-A25 beads ($\sim$100 micron diameter), it will usually be sufficient to use from 10 to 50 of the beads to adsorb labelled probe from 20-50 $\mu$l of solution (probe originally hybridized to a two millimeter diameter sample dot on a nitrocellulose filter). Usually about 50% or more of the labelled probe can be adsorbed onto the beads in less than one hour. In the case of using 10 beads, about a 40 fold concentration of labeled probe is achieved in moving it from the 2 millimeter nitrocellulose sample dot (area $\sim 1 \times 10^5$ square microns). With the probe in a 50 $\mu$l volume ($5 \times 10^{10}$ cubic microns) solution adsorption to 10 beads ($1 \times 10^7$ cubic microns) produces a 5000 fold concentration effect in terms of volume. In general, the smaller the number of beads or surface area the probe is finally adsorbed to the better. However, for any given number of beads there is a limitation of the probe transfer rate to the beads as the volume of the solution increases. Since the adsorbent materials are ion-exchangers, efficiency for binding probes will decrease as ionic strength of the solutions increases, therefore solutions should be kept as diluted as possible ($\leq 0.4$M NaCl and $\leq 0.02$M for phosphate and citrate buffers). In general, extremes of temperature or pH should be avoided with regard to adsorption of labelled probe to beads. Temperatures higher than $\sim 40°$ C. and pH's lower than 5 should be avoided in particular.

It is within the scope of this invention to employ other methods for concentrating and/or increasing the transfer rate of the dehybridized probe to adsorbent materials. For example, the solution containing the probe may be concentrated by evaporation, flocculation or precipitation. These and similar procedures can result in concentration and focusing of the dehybridized probe permitting improved fluorescent analysis. With regard to increasing or improving the transfer rate of labelled probe in solution to the adsorbent material, general procedures include agitation and mixing of the adsorbent beads with the labelled probe solution or the flowing of the labelled probe solution through an aggregation of the adsorbent material in a small orifice. Also, it is possible to electrofocus the labelled probe onto a small area using microelectrophoresis.

After the dehybridized probe has been adsorbed and concentrated, such as on the adsorbent beads described above, it can be examined by standard procedures for detecting the particular label or reporter group associated with the probe. Where the probe, as preferred, is labelled with a fluorescent group, the beads may be examined with an epifluorescent microscope or other fluorescent analysis system designed for ultrasensitive detection. Usually the analysis and quantitation takes only a matter of minutes for a given sample.

The method of this invention can be further understood in relation to the following examples.

EXAMPLE I

The following example demonstrates the advantage for detecting fluorescent probes concentrated onto suitable materials, like Sephadex QAE A-25 beads, over observing the same probe bound to nitrocellulose filter material. The fluorescent probe used in these experiments was a 22-mer sequence specific for a genomic target sequence present in Herpes Simplex Virus (HSV). The probe was labeled with a Texas Red fluorophore group having an excitation and emission maxima at 596 nm and 620 nm respectively. The labeled probe was designated TR-HSV, and the sequence and position of the label are shown below:

5'-CCCGAGCCGATGACTTACTGGC—3'

The first experiment involved the epifluorescent analysis of the TR-HSV probe bound to nitrocellulose filters. A 10-fold dilution series of TR-HSV probe ranging from $2 \times 10^{-12}$ to $2 \times 10^{-18}$ mole per microliter of 1X SSPE buffer was prepared. One microliter of each dilution was adsorbed onto nitrocellulose filter material forming a 2–3 millimeter diameter spot. A control spot of 1 μL of 1×SSPE (no probe) was also prepared. The spots were now analyzed by using a photon counting epifluorescent microscope filtered for Texas Red fluorescence (Ex ~550 nm; Em ~630 nm). The fluorescent signal from each sample spot was counted (EG&G Photon Counting System) for one second (each sample spot was counted twice). Results for the analysis are shown in Table I. Since only 1/10 the area of each spot was analyzed (10× microscope field), samples 1 through 7 ranges from $2 \times 10^{-13}$ to $2 \times 10^{-19}$ mole in actual TR-HSV probe concentration.

TABLE I

| | TR-HSV Probe/Nitrocellulose Filter | |
|---|---|---|
| Sample | TR-HSV (mole)* | Avg. Counts (1 second) |
| 1 | $2 \times 10^{-13}$ | $1.5 \times 10^6$ |
| 2 | $2 \times 10^{-14}$ | 157,429 |
| 3 | $2 \times 10^{-15}$ | 27,918 |
| 4 | $2 \times 10^{-16}$ | 26,246 |
| 5 | $2 \times 10^{-17}$ | 21,155 |
| 6 | $2 \times 10^{-18}$ | 22,100 |
| 7 | $2 \times 10^{-19}$ | 23,397 |
| Control | — | 22,399 |

*Concentration in area observed

The results in Table I show that fluorescence from the TR-HSV probe can be detected down to about $2 \times 10^{-16}$ mole (sample 4) on nitrocellulose filter material.

The second experiment involved the epifluorescent analysis of the TR-HSV probe bound to QAE-Sephadex A-25 beads. A 10-fold dilution series of TR-HSV probe ranging from $4 \times 10^{-11}$ to $4 \times 10^{-17}$ mole per 10 microliters of 1X SSPE buffer was prepared. Approximately 1000 QAE-Sephadex A-25 beads (previously swollen in 1X SSPE buffer) were added to each of the sample dilutions. A control sample of beads with no TR-HSV probe was also prepared. The samples were allowed to stand for about one hour with intermittent gentle agitation. Samples were then analyzed using the photon counting epifluorescent microscope. In this experiment, the fluorescence from individual beads in each sample were counted. The results in Table 2 are the average counts (one second) from two beads in each sample counted twice. The results are given in terms of TR-HSV concentration per bead, i.e., it is assumed most of the probe has adsorbed evenly to all the beads in the sample.

TABLE 2

| | TR-HSV Probe/QAE-Sephadex A-25 | |
|---|---|---|
| Sample | TR-HSV (mole)/bead | Avg. Counts (1 second) |
| 1 | $4 \times 10^{-14}$ | $9 \times 10^6$ |
| 2 | $4 \times 10^{-15}$ | 645,867 |
| 3 | $4 \times 10^{-16}$ | 43,229 |
| 4 | $4 \times 10^{-17}$ | 15,614 |
| 5 | $4 \times 10^{-18}$ | 13,581 |
| 6 | $4 \times 10^{-19}$ | 5,429 |
| 7 | $4 \times 10^{-20}$ | 4,782 |

TABLE 2-continued

| | TR-HSV Probe/QAE-Sephadex A-25 | |
|---|---|---|
| Sample | TR-HSV (mole)/bead | Avg. Counts (1 second) |
| Control | — | 4,320 |

The results in Table 2 show that fluorescence from the TR-HSV probe at $4 \times 10^{-20}$ mole per bead still has counts significantly higher than the control beads (no probe).

The third experiment is basically a complete repeat of the second experiment. The results are given in Table 3.

TABLE 3

| | TR-HSV Probe/QAE Sephadex A-25 | |
|---|---|---|
| Sample | TR-HSV (mole)/bead | Avg. Counts (1 second) |
| 1 | $4 \times 10^{-14}$ | $1 \times 10^7$ |
| 2 | $4 \times 10^{-15}$ | $1 \times 10^6$ |
| 3 | $4 \times 10^{-16}$ | 85,939 |
| 4 | $4 \times 10^{-17}$ | 17,022 |
| 5 | $4 \times 10^{-18}$ | 13,627 |
| 6 | $4 \times 10^{-19}$ | 10,182 |
| 7 | $4 \times 10^{-20}$ | 8,082 |
| Control | — | 7,341 |

The results in Table 3 show again that fluorescence from the TR-HSV probe at $4 \times 10^{-20}$ mole per bead has counts significantly (~10%) higher than the control beads. The higher counts for control beads in experiment 3 (7,341) compared to experiment 2 (4,320) are due to the higher excitation intensity used in this experiment.

In summary, TR-HSV probe can be detected down to about $4 \times 10^{-20}$ mole on a single bead of QAE-Sephadex A-25 by epifluorescence analysis. On nitrocellulose filter material it can be detected down to only about $2 \times 10^{-16}$ mole.

EXAMPLE II

In further experiments similar to those described in Example 1 it was demonstrated that another type of fluorescent probe (Fluorescein labelled) can be concentrated and more favorably detected on QAE-Sephadex A-25 beads. Also, it is shown that other supports, such as QAE Controlled Pore Glass Beads, work favorably.

The first experiment involves the epifluorescent analysis of a fluorescein labelled HSV probe (F-HSV) bound to Zeta Bind (nylon) filter material. The F-HSV probe is exactly the same as the TR-HSV probe except for the different fluorophore label. The fluorescein label has its excitation and emission maximum at ~490 nm and ~520 nm respectively. The experiment with F-HSV probe adsorbed to Zeta Bind was carried out exactly like the first experiment in Example I. However, the photon counting epifluorescence microscope was filtered for fluorescein fluorescence (Ex ~450 nm, Em ~520 nm). Results for the analysis are shown in Table 4.

TABLE 4

| | F-HSV Probe/Zeta Bind Filter | |
|---|---|---|
| Sample | F-HSV (mole)* | Avg. Counts (1 second) |
| 1 | $6 \times 10^{-13}$ | 843,568 |
| 2 | $6 \times 10^{-14}$ | 200,248 |
| 3 | $6 \times 10^{-15}$ | 55,914 |
| 4 | $6 \times 10^{-16}$ | 45,587 |

TABLE 4-continued

| F-HSV Probe/Zeta Bind Filter | | |
|---|---|---|
| Sample | F-HSV (mole)* | Avg. Counts (1 second) |
| Control | — | 47,675 |

*Concentration in area observed.

The results from Table 4 show that fluorescence at $\sim 6 \times 10^{-15}$ mole of probe is just distinguishable from the control sample.

The second experiment involves the epifluorescent analysis of the F-HSV probe bound to QAE-Sephadex A-25 beads. This experiment was carried out in a manner similar to the second experiment in Example I. Results for the analysis are shown in Table 5.

TABLE 5

| F-HSV Probe/QAE-Sephadex Beads | | |
|---|---|---|
| Sample | F-HSV (mole)/bead | Avg. Counts (1 second) |
| 1 | $7 \times 10^{-14}$ | $10^7$ |
| 2 | $7 \times 10^{-15}$ | $2 \times 10^6$ |
| 3 | $7 \times 10^{-16}$ | 136,736 |
| 4 | $7 \times 10^{-17}$ | 56,924 |
| 5 | $7 \times 10^{-18}$ | 31,401 |
| 6 | $7 \times 10^{-19}$ | 32,194 |
| Control | — | 27,507 |

The results from Table 5 show that fluorescence from the F-HSV probe is detectable at the $7 \times 10^{-18}$ mole per bead level.

As was the case with the TR-HSV probe (Example I), the F-HSV probe is significantly more detectable on QAE-Sephadex A-25 beads than on Zeta Bind filter material.

The third experiment involves the epifluorescent analysis of TR-HSV probe bound to QAE-Controlled Pore Glass beads. This experiment was carried out similar to the others described above. Results for the analysis are shown in Table 6.

TABLE 6

| TR-HSV Probe/QAE-Controlled Pore Glass Beads | | |
|---|---|---|
| Sample | TR-HSV Probe/Bead | Avg. Counts (1 second) |
| 1 | $4 \times 10^{-14}$ | $10^7$ |
| 2 | $4 \times 10^{-15}$ | $2 \times 10^6$ |
| 3 | $4 \times 10^{-16}$ | 179,131 |
| 4 | $4 \times 10^{-17}$ | 51,797 |
| 5 | $4 \times 10^{-18}$ | 20,454 |
| 6 | $4 \times 10^{-19}$ | 16,897 |
| 7 | $4 \times 10^{-20}$ | 15,497 |
| Control | — | 11,930 |

The results from Table 6 show that TR-HSV probe is detectable to the $4 \times 10^{20}$ mole level on individual QAE-Controlled Pore Glass beads.

EXAMPLE III

The experiment described below demonstrates that fluorescent probe actually hybridized to a target DNA sequence immobilized on a polystyrene bead support material (not suitable for fluorescent analysis) can be dehybridized and concentrated onto QAE-Sephadex A-25 beads for epifluorescent analysis. In this experiment the TR-HSV probe used was also labelled with $^{32}$Phosphorous radioisotope ($^{32}$P). Thus a comparison could be made between the fluorescent and radioisotope level of detection.

Using one milligram samples of polystyrene beads ($\sim 1$-2 micron diameter, substituted with a complementary target sequence), a 10-fold dilution series of $^{32}$P-TR-HSV probe ranging from $\sim 1 \times 10^{-13}$ to $\sim 1 \times 10^{-18}$ mole in 50 $\mu$l of 5X SSPE hybridization buffer were prepared (control sample contained no probe). The samples were hybridized for 30 minutes at 40° C., then centrifuged and supernatant removed. The samples were then washed three times with 5X SSPE. After the final wash and removal of supernatant, 10 $\mu$l of 6M Urea (1X SSPE) was added to each of the samples in order to dehybridize the probe from the support. Dehybridization was carried out for about 30 minutes at room temperature. At this point the polystyrene beads were separated from the solution containing dehybridized $^{32}$P-TR-HSV probe by centrifugation. To this solution between 20 to 30 QAE-Sephadex A-25 beads were added. The dehybridized probe was allowed to adsorb to the QAE-Sephadex beads for about 30 minutes. At this point the QAE-Sephadex A-25 beads were separated from the solution. The beads (all 20 to 30) were first counted on a scintillation counter (one minute counts) to determine level of probe finally transferred to the QAE-Sephadex A-25 beads by radioisotope method. After scintillation counting individual beads were counted on the photon counting epifluorescent microscope to determine sensitivity by fluorescence. The results for each type of analysis are shown in Table 7.

TABLE 7

| $^{32}$P-Tr-HSV Transfer to QAE-Sephadex | | | | |
|---|---|---|---|---|
| Sample | Total Conc. $^{32}$P-Tr-HSV Probe | $^{32}$P Counts | $^{32}$P-Tr-HSV Conc. per bead | Fluorescent Counts (1 sec.) |
| 1 | $\sim 6 \times 10^{-15}$ | 7460 | $\sim 3 \times 10^{-16}$ | 104,572 |
| 2 | $\sim 6 \times 10^{-16}$ | 951 | $\sim 3 \times 10^{-17}$ | 28,847 |
| 3 | $\sim 6 \times 10^{-17}$ | 159 | $\sim 3 \times 10^{-18}$ | 13,704 |
| 4 | $\sim 6 \times 10^{-18}$* | 43 | $\sim 3 \times 10^{-19}$ | 13,170 |
| 5 | $\sim 6 \times 10^{-19}$* | 40 | $\sim 3 \times 10^{-20}$ | 10,227 |
| Control | — | 44 | — | 8,900 |

*extrapolated

The results in Table 7 show that about $6 \times 10^{-17}$ mole of $^{32}$P-TR-HSV probe transferred to QAE-Sephadex beads could be detected by radioisotope counting ($^{32}$P, 1 minute count) before control or background level is reached ($\sim 44$ counts). Fluorescent counts were found to be above the control through the whole sample series 1→5. When considered in terms of individual beads, on the order of $10^{-20}$ mole of $^{32}$P-TR-HSV probe was detectable.

EXAMPLE IV

The following experiment demonstrates the usefulness of a so-called "displacer probe" in effecting the dehybridization of a fluoresence labelled probe hybridized to target DNA immobilized on a support material.

In this experiment $^{32}$P-TR-HSV probe was hybridized to plasmid target DNA (pHSV106) immobilized onto nitrocellulose filter material. The pHSV106 plasmid DNA was immobilized onto the nitrocellulose filter using the Hybrid-Dot apparatus and experimental procedure described earlier in this patent application. The concentrations of pHSV106 plasmid DNA in each "dot" ($\sim 2$ millimeter diameter spot) were (1) 100 ng; (2) 10 ng, (3) 1 ng, (4) 100 pg, and (5) control (non-target DNA). $^{32}$P-TR-HSV probe was hybridized to the pHSV106 target dots by the procedures discussed earlier in this application. After hybridization and appropriate washing, the level of $^{32}$P-TR-HSV probe hybridized to each "dot" was measured by a scintillation counter. The results are given in Table 8. After counting, the dehybridization procedure was carried out using a specific displacer probe for the $^{32}$P-TR-HSV probe. The sequence of the displacer probe is given below:

5'—CCCGAGCCGATGACTTACTG-
<u>GCAGGTGCTGGGGG</u>—3'

The portion of the displacer probe underlined is identical to that of the $^{32}$P-TR-HSV probe. Dehybridization of $^{32}$P-TR-HSV/pHSV106 target DNA nitrocellulose "dots" was carried out by treating each one of the sample "dots" with 50 μl of 1X SSC buffer solution containing approximately 100 ng of the displacer probe for 30 minutes at ~25° C. The nitrocellulose filter "dots" were then separated from the solution and each solution and "dot" sample was counted on the scintillation counter. The results are given in Table 8.

TABLE 8

Displacer Probe Experiment

| Sample (pHSV106) | 1st Count (1 min.) after Hybridization & Wash | 2nd counts (1 min) After Displacer Probe | |
|---|---|---|---|
| | | Filter "Dots" | Solution |
| 1  100 ng | 39,672 | 5,969 | 32,353 |
| 2  10 ng | 5,805 | 1,347 | 4,296 |
| 3  1 ng | 1,702 | 1,113 | 754 |
| 4  100 pg | 1,543 | 1,109 | 706 |
| 5  None | 1,296 | 1,210 | 198 |

The results in Table 8 show that the "displacer probe" treatment has successfully dehybridized the $^{32}$P-TR-HSV probe from the pHSV106 target/nitrocellulose filter "dots."

I claim:

1. The hybridization assay method for detecting a specific polynucleotide target sequence wherein a nucleic acid containing target sample in single stranded form is affixed to a support, contacted thereon under hybridizing conditions with a non-radioactive reporter group labeled single-stranded polynucleotide probe having a sequence complementary to the target sequence, said probe being bound to said affixed sample when the target is present, said probe hybridizing with said target sequence, then removing the unbound portion of said probe from said support, and detecting the presence of said probe by means of its reporter group, wherein the sensitivity of the assay is increased by employing the additional steps comprising:

(a) after removal of the unbound portion of the probe, dehybridizing the bound portion;
(b) concentrating the dehybridized separated probe onto a solid support; and
(c) detecting the presence of said probe on said solid support by means of said non-radioactive reporter group.

2. The method of claim 1 in which the dehybridized portion of the probe is concentrated by adsorption from an aqueous solution onto a basic anion exchange material binding said probe.

3. The method of claim 2 in which the anion exchanger functional groups are quaternary amino groups.

4. The method of claim 3 in which said anion exchange functional groups are provided on a substrate selected from cross-linked dextran or glass.

5. The method of claim 1 in which the bound labelled probe portion is dehybridized by contacting the supported sample with a displacer probe comprising a single stranded polynucleotide sequence longer than the labelled probe including the same sequence as the labelled probe and an additional sequence complementary to the sequence of said target sample adjacent said target sequence to which the labelled probe is bound, said additional sequence being of sufficient length to cause said displacer to preferentially bind to said target sequence and subsequently displace said labelled probe therefrom.

6. A hybridization assay method for detecting a specific target sequence wherein a nucleic acid sample in single-stranded form is affixed to a support, contacted thereon with a non-radioactively labelled polynucleotide probe having a single-stranded sequence complementary to the target sequence to be directed, said probe comprising a sequence of 10 to 50 nucleotide units and having a reporter group attached thereto, said probe being bound to said affixed sample when the specific target is present, removing the unbound portion of said probe from said support, and detecting the presence of said probe by means of its reporter group, wherein the sensitivity to the assay is increased by employing the additional steps comprising:

(a) after removal of the unbound portion of the probe, dehybridizing the bound portion and forming an aqueous solution thereof;
(b) contacting the separated solution with an anion exchange material for binding said probe so as to concentrate said probe onto the anion exchange material; and
(c) detecting its presence on said anion exchange material by means of said non-radioactive reporter groups.

7. The method of claim 6 in which said anion exchange material comprises an adsorbent substrate selected from cross-linked dextran or glass with substituted amino groups attached thereto.

8. The method of claim 6 in which said probe is labelled with a fluorescent reporter group.

9. The method of claim 6 in which the bound probe portion is dehybridized by contacting the supported sample with a displacer probe comprising a single-stranded polynucleotide sequence longer than the labelled probe including the same sequence as the probe and an additional sequence complementary to the sequence of said target sample adjacent said target sequence to which the probe is bound, said additional sequence being of sufficient length to cause said displacer to preferentially bind to said target sequence and displace said probe therefrom.

10. The hybridization assay method for detecting a specific polynucleotide target sequence wherein a nucleic acid sample containing target in single-stranded form is affixed to a support, contacted thereon under hybridizing conditions with a polynucleotide probe having a single-stranded sequence complementary to a characterizing target sequence to be detected, said probe comprising a sequence of from 10 to 50 nucleotide units and having a fluorescent label attached thereto, probe being bound to said affixed sample when the specific target is present, said complementary sequence of the probe hybridizing with said target sequence, removing the unbound portion of said portion of said probe from said support, and detecting the presence of said probe by means of its reporter group, wherein the sensitivity of the assay is increased by employing the additional steps comprising:

(a) after removal of the unbound portion of the probe, dehybridizing the bound portion of the probe and forming an aqueous solution thereof;
(b) contacting the separated solution with an anion exchange material comprising a substrate selected from cross-linked dextran or glass with substituted amino group provided thereon so as to concentrate the probe on said anion exchange material; and
(c) detecting the presence of said probe on said anion exchange material by means of said fluorescent label.

11. The method of claim 10 in which said anion exchange material is in the form of porous generally spherical beads.

12. The method of claim 10 in which the bound labelled probe portion is dehybridized by contacting the supported sample with a displacer comprising a single stranded polynucleotide sequence longer than the labelled probe including the same sequence as the labelled probe and an additional sequence complementary to the sequence of said target sample adjacent said target sequence to which the probe is bound, said additional sequence being of sufficient length to cause said displacer to preferentially bind to said target sequence and displace said probe therefrom.

13. The method of claim 10 in which said anion exchange material comprises porous beads of cross-linked dextran having substituted amino groups attached thereto.

14. The method of claim 10 in which said anion exchange material comprises porous beads of silica glass having substituted amino groups attached thereto.

* * * * *